United States Patent
Gouldson

(12) 
(10) Patent No.: US 6,715,650 B2
(45) Date of Patent: *Apr. 6, 2004

(54) GARMENT HANGER

(75) Inventor: Stanley F. Gouldson, Northport, NY (US)

(73) Assignee: Spotless Plastics Pty. Ltd., Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 10/237,818

(22) Filed: Sep. 9, 2002

(65) Prior Publication Data

US 2003/0015485 A1 Jan. 23, 2003

Related U.S. Application Data

(63) Continuation of application No. 10/077,296, filed on Feb. 15, 2002, now Pat. No. 6,467,659, which is a continuation of application No. 09/739,568, filed on Dec. 18, 2000, now Pat. No. 6,357,638, which is a continuation-in-part of application No. 08/867,986, filed on Jun. 3, 1997, now Pat. No. 6,196,430, which is a continuation of application No. 08/675,228, filed on Jul. 1, 1996, now abandoned, which is a continuation-in-part of application No. 29/054,319, filed on May 9, 1996, now Pat. No. Des. 392,113.

(51) Int. Cl.[7] .............................................. A41D 27/22
(52) U.S. Cl. ......................................... 223/93; 223/96
(58) Field of Search ....................................... 223/96, 93

(56) References Cited

U.S. PATENT DOCUMENTS

| | | |
|---|---|---|
| 119,938 A | 10/1871 | Mellish |
| 143,024 A | 9/1873 | Mellish |
| 491,062 A | 1/1893 | Granger |
| D33,665 S | 12/1900 | Kramer |
| 697,103 A | 4/1902 | Pickhardt |
| 723,587 A | 3/1903 | Cowles |
| 769,694 A | 9/1904 | Geisert |
| 1,315,823 A | 2/1919 | Dugan |
| 1,447,083 A | 2/1923 | Jonas |
| 1,605,918 A | 11/1926 | Buchanan |
| 2,095,900 A | 10/1937 | Albert |

(List continued on next page.)

FOREIGN PATENT DOCUMENTS

| | | |
|---|---|---|
| AU | 401137 | 9/1966 |
| DE | 1775341 | 6/1958 |
| DE | 7613691 | 10/1976 |
| DE | 7636729 | 3/1977 |
| FR | 974290 | 10/1918 |
| FR | 1424774 | 2/1965 |
| GB | 910375 | 10/1959 |
| GB | 115472 | 4/1967 |
| GB | 1514978 | 12/1975 |
| GB | 2069332 | 2/1980 |
| GB | 2058192 | 7/1980 |
| WO | 97/07434 | 1/1998 |

*Primary Examiner*—John J. Calvert
*Assistant Examiner*—James G Smith
(74) *Attorney, Agent, or Firm*—Scully, Scott, Murphy & Presser

(57) ABSTRACT

A molded plastic garment hanger as is widely used for the purpose of shipping and displaying garments, comprising a unitary plastic central hook and arms extending in opposite directions from the base of the central hook to facilitate a garment to be suspended therefrom by garment clips. The garment clips enable the attachment of various kinds of garments thereto, such as underwear, slips, brassieres, swimwear and the like, and are particularly adapted to secure the shoulder straps of such garments. The garment hanger has an improved garment retaining clip wherein as a garment strap is inserted into the garment retaining clip, the garment receiving channel of the clip first opens to allow the garment strap to enter, and then closes to securely retain the garment and to prevent it from becoming accidentally dislodged therefrom.

17 Claims, 7 Drawing Sheets

U.S. PATENT DOCUMENTS

| | | |
|---|---|---|
| 2,107,026 A | 2/1938 | Coney |
| 2,145,120 A | 1/1939 | Loveless |
| 2,171,680 A | 1/1939 | Baugh |
| D122,692 S | 2/1940 | Owen |
| 2,318,084 A | 5/1943 | LaPorte |
| 2,393,632 A | 1/1946 | Hartz |
| 2,401,413 A | 6/1946 | Colwell |
| 2,421,307 A | 1/1947 | Albrecht |
| 2,419,723 A | 4/1947 | Mack |
| 2,471,141 A | 5/1949 | Castelli |
| 2,492,287 A | 12/1949 | Hogan |
| D159,252 S | 7/1950 | Cook |
| D167,986 S | 3/1952 | Jonaitis |
| 2,620,103 A | 11/1952 | Antolini |
| 2,723,787 A | 11/1955 | Bransdorf |
| 2,908,431 A | 10/1959 | Campbell |
| 3,028,974 A | 4/1962 | Loeb |
| 3,041,696 A | 12/1962 | Ferri |
| D194,726 S | 2/1963 | Allen |
| 3,076,242 A | 2/1963 | Priolo |
| D196,496 S | 10/1963 | Kennedy |
| 3,209,966 A | 10/1965 | Wach |
| 3,225,977 A | 12/1965 | Gandy |
| D204,134 S | 3/1966 | Duncan |
| 3,327,912 A | 6/1967 | Blair |
| 3,405,429 A | 10/1968 | Vasquez |
| D214,968 S | 8/1969 | Field et al. |
| 3,463,369 A | 8/1969 | Moskowitz |
| 3,464,605 A | 9/1969 | Apel |
| 3,524,226 A | 8/1970 | Brown |
| D219,488 S | 12/1970 | Schayer |
| 3,570,729 A | 3/1971 | Zuckerman |
| 3,738,549 A | 6/1973 | Driscoll |
| D236,572 S | 9/1975 | Ostroll |
| D244,197 S | 5/1977 | Ostroll |
| D246,817 S | 1/1978 | Mainetti |
| 4,132,316 A | 1/1979 | Schmidt |
| 4,148,421 A | 4/1979 | Levitt |
| D258,336 S | 2/1981 | Yacoe |
| D264,912 S | 6/1982 | Bliss |
| D264,913 S | 6/1982 | Bliss et al. |
| 4,623,079 A | 11/1986 | Tendrup et al. |
| 4,629,102 A | 12/1986 | Tendrup et al. |
| 4,714,183 A | 12/1987 | Tontarelli |
| 4,828,155 A | 5/1989 | Louw |
| D305,484 S | 1/1990 | Fildan |
| 4,892,237 A | 1/1990 | Duester et al. |
| 4,951,855 A | 8/1990 | Jacobson et al. |
| 5,002,210 A | 3/1991 | Kolton et al. |
| 5,062,556 A | 11/1991 | Willputz |
| 5,065,916 A | 11/1991 | Fildayniski |
| 5,127,559 A | 7/1992 | Freer et al. |
| 5,129,557 A | 7/1992 | Kolton et al. |
| 5,236,109 A | 8/1993 | Zuckerman |
| D340,586 S | 10/1993 | Fildan |
| 5,411,189 A | 5/1995 | Gouldson |
| 5,509,587 A | 4/1996 | Gouldson et al. |
| 5,516,013 A | 5/1996 | Gouldson et al. |
| D371,246 S | 7/1996 | Gouldson et al. |
| D377,717 S | 2/1997 | Gouldson |
| 5,632,423 A | 5/1997 | Louw |
| D381,814 S | 8/1997 | Louw |
| D388,620 S | 1/1998 | Gouldson et al. |
| D388,964 S | 1/1998 | Gouldson |
| D390,015 S | 2/1998 | Gouldson |
| D392,113 S | 3/1998 | Gouldson |
| 5,775,553 A | 7/1998 | Marshall et al. |
| 6,196,430 B1 * | 3/2001 | Gouldson ............ 223/96 |
| 6,357,638 B2 * | 3/2002 | Gouldson ............ 223/96 |
| 6,467,659 B2 * | 10/2002 | Gouldson ............ 223/96 |

* cited by examiner

Figure 3
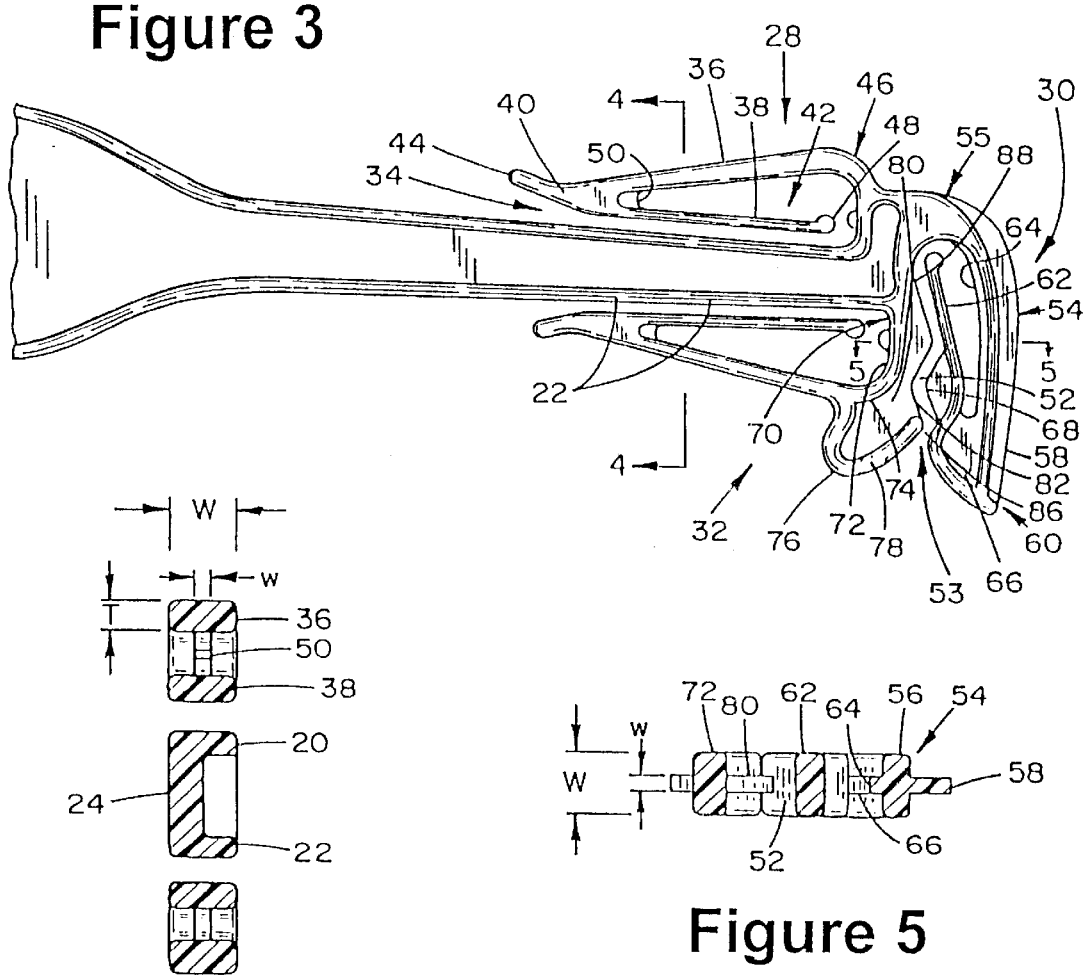
Figure 4
Figure 5
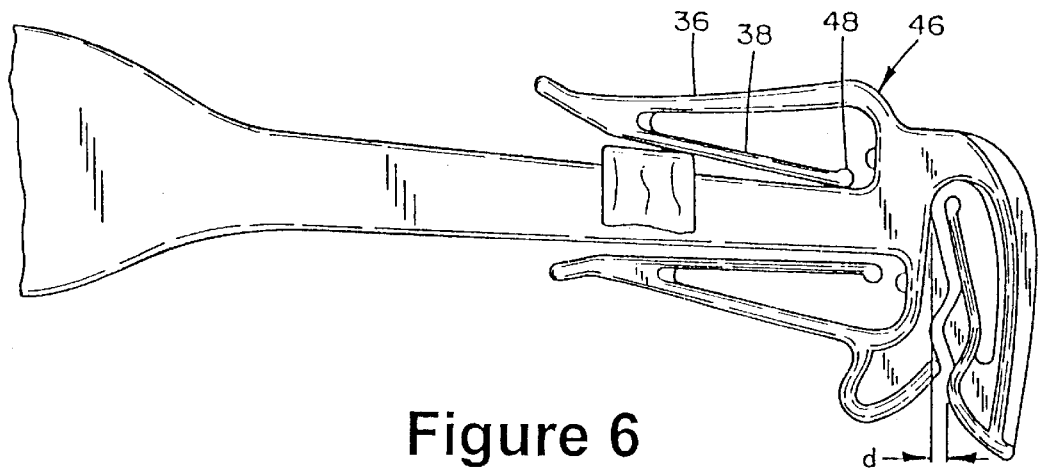
Figure 6

GARMENT HANGER

CROSS REFERENCE TO RELATED APPLICATION

This patent application is a continuation of Ser. No. 10/077,296, filed Feb. 15, 2002, now U.S. Pat. No. 6,467,659, which is patent application Ser. No. 09/739,568, now U.S. Pat. No. 6,357,638, filed on Dec. 18, 2000 which is a continuation-in-part of patent application Ser. No. 08/867,986, now U.S. Pat. No. 6,196,430, filed Jun. 3, 1997, which is a continuation of patent application Ser. No. 08/675,228, abandoned, filed Jul. 1, 1996 which is a continuation-in-part of patent application Ser. No. 29/054,319, now U.S. Pat. No. Des. 392,113 for a GARMENT HANGER, filed May 9, 1996.

BACKGROUND OF THE INVENTION

1. Field of the Invention

The present invention relates generally to molded plastic garment hangers as are widely used for the purpose of shipping and displaying garments. Garment hangers of that type may be simply constructed as molded plastic structures incorporating a central hook adapted to be suspended from a suitable support, such as a garment display rack or the like. The garment hanger body typically has arms extending in opposite directions from the base of the central hook so as to facilitate a garment to be suspended therefrom. The opposite or distal ends of the arm typically have garment clips formed thereon to enable the attachment of various kinds of garments thereto, such as underwear, slips, brassieres, swimwear, multiple garments, and the like.

2. Discussion of the Prior Art

A wide variety of molded plastic garment hangers with garment clips are presently known. U.S. Pat. No. 5,632,423 discloses a Garment Hanger having plural garment retaining clips on the distal ends of the arm, with improvements to the design of the clip, which was previously described in U.S. Pat. No. 4,828,155. One of the improvements described in this patent is the addition of a stop formation which is "substantially aligned" with the elongated pressing member which engages the garment to be hung from the hanger. The stop formation is intended to prevent the strap of a brassier from sliding around the end of the pressing member into the open and enclosed space above the elongated pressing member. This stop formation is disclosed in FIGS. 9(a), (b) of this application, which correspond to FIGS. 19 and 21 of U.S. Pat. No. 5,632,423, a known prior art design.

U.S. Pat. Nos. 4,623,079 and 4,629,102 disclose a hanger having an elevated hook member, a hanger body having horizontally extending arms and respectively, resilient grips and clips of a U-shaped configuration located at the end of each arm. The U-shaped configuration includes first and second members, which are also being connected to each other; the second member also being connected to the hanger body. The U-shaped garment engaging clip has a double-flex mechanism to prevent breakage of the clip when a garment is resiliently engaged.

U.S. Pat. No. 4,892,237 discloses a plastic garment hanger having a hook, a body bar extending longitudinally from the hook, with the body bar terminating at each end in a pair of arms, one above and one below the body bar which form garment receiving slots. A third arm creates a downwardly opening slot at the end of the body. The shape of the arms is such that the mouth or open end of the slot is narrower than the upper or inner end of each clip. Adjacent the blind end of the garment receiving slot, the slot is deepened to form a pocket which is recessed downwardly into the body. At the entrance of the pocket a tongue from the upper flange of the body bar is provided. The tongue divides the pocket. Additionally, a finger which extends upwardly and outwardly at an angle from the upper flange of the body bar is provided. The finger is spaced inwardly a short distance from the clip.

U.S. Pat. No. 5,065,916 discloses a plastic garment hanger having garment retaining clip ends formed with downwardly and outwardly included support elements from which upper and lower retaining elements extend in a "T" and are provided directly with the formations engaging the garments in respective channels. The channels are defined by a surfaces having inter-digitating arrays of teeth. The clip configuration is intended to overcome the deficiencies ordinary associated with clips having flexible bent back finger.

U.S. Pat. No. 5,129,557 discloses a plastic garment hanger having a hook, a body bar extending longitudinally from the hook and wing portions terminating each end of the body bar. Each wing portion defines a second channel in intersecting relation with the first channel. The second channel is inclined at an acute angle with respect to the first channel. Positioned along the first channel are a series of generally semi-circular projections which function to impede the movement of the garment, i.e. panty, intended to be suspended therefrom.

U.S. Pat. No. 5,236,109 discloses a plastic, multi-garment hanger which includes a slot extending upwardly from the edge of the body member between a vertically oriented clip and a horizontally oriented clip. The slot provides for the displacement of a portion of the vertically oriented clip and/or the horizontally oriented clip thereby reducing the level of stress concentrated at the upper, inward edge of vertical oriented clips and the connecting portion of the horizontally oriented clips of the typical multi-clip hangers. However, while the slot is taught to provide additional flexibility, applicant notes that the portions of the vertically oriented and horizontally oriented clips of U.S. Pat. No. 5,236,109 are necessarily thinner in construction which weakens such clips and reduces their strength.

Each of the above-described prior art hangers (with the exception of the hanger provided by U.S. Pat. No. 5,129,557) is provided with a clip arrangement for the retention of light-weight, two-piece garments, such as panties and brassieres. Each type of clip arrangement is provided with some level of flexibility necessary for the insertion of the garment clip.

Other typical prior art hangers are exemplified by U.S. Pat. Nos. 4,623,079; 4,629,102; 4,892,237; 5,065,916; and 5,129,557 and Des. 246,817.

The clip arrangement of the hanger discloses in U.S. Pat. No. 4,623,079 and 4,629,102, described above, has generally a U-shaped configuration, the flexible free end of which can be deflected in two directions.

A problem in the prior art with the molded plastic garment hangers having U-shaped clips illustrated in U.S. Pat. Nos. 4,623,079, 4,629,102, 4,828,155 and 5,632,423 is encountered when brassieres having thin straps are suspended from the hanger. These thin straps, particularly those supporting sheer brassieres, have a tendency to slip around the end of the inner member of the U-shaped clip, and get caught in the inner space of the unshaped clip. While the stop formations described in U.S. Pat. No. 5,632,423 were intended to stop this problem, the problem still persists. Once the strap has migrated into this position, it is difficult to remove the strap from within the clip without damaging the clip or the garment strap.

SUMMARY OF THE INVENTION

Accordingly, it is a primary object of the present invention to provide garment hangers having improved garment retaining clips at opposite ends thereof which are designed to securely retain a garment to prevent it from being accidentally dislodged therefrom. Moreover, the improved garment retaining clips are designed to avoid breakage of the clips, and to prevent the migration of brassier straps around the ends of the inner arms of the clips into the inner free space of the clip. The present invention solves this problem by providing an improved stop formation which is not "substantially aligned" when the clip is at rest, but which is aligned when the inner arm of the clips have been displaced by the brassiere strap.

Further, the improved garment clips of the present invention are designed with a much greater flexibility, without a stiffening rib extending longitudinally along the outer length of the moveable clip arm. The more flexible clip arm is much easier to open and use, and moreover the greater flexibility also makes the insertion of garments, particularly thicker garments, into the clips much easier, and greatly alleviates problems with carpel tunnel syndrome by persons who are employed to insert a great number of garments into a great number of such garment retaining clips.

A further object of the subject invention is the provision of a garment hanger having an improved garment retaining clip wherein as a garment is inserted into the garment retaining clip, a compound movement and action of first and second support members arranged in a double return configuration result in the garment receiving channel of the clip first opening to allow the garment to enter, and then closing to securely retain the garment therein and to prevent it from becoming accidentally dislodged therefrom.

The garment hanger also has an improved panty retaining clip having an inward slant defined by a receiving channel of the panty retaining clip. As a panty waist band is inserted into the panty retaining clip and is inserted from an initial position at an opening thereof to a fully inserted position, the panty waist band moves radially inwardly towards the center of the garment hanger. Accordingly, after a panty waist band is inserted fully into the panty retaining clip, the panty waist band shrinks at each end of the garment hanger. This also means that the panty waist band must be expanded or stretched at each end of the garment hanger to remove the panty from the panty retaining clip, which makes accidental removal or dislodgement of the garment from the garment clip a virtual impossibility.

In accordance with the teachings herein, the present invention provides a lightweight, molded plastic garment hanger comprising a hook member and a body member extending longitudinally from the hook member. The body member defines first and second opposite ends, and a garment retaining clip is integrally molded with the body member at each of the first and second ends. Each garment retaining clip is positioned adjacent to the body member, and defines a garment receiving channel therebetween. The garment retaining clip defines a compound movement, double return configuration formed by a first member mounted to the end of the body member by a first cantilever mount and having a spaced end, and a second member integrally connected in a spaced relation to the first member by a second cantilever mount and having a spaced free end. As a garment enters the garment receiving channel, an initial expansion at the mouth of the garment receiving channel causes a rotation of the combination of the first and second members about the first cantilever mount. Subsequently as the garment slides past the second cantilever mount, it causes an upward flexure of the free end of the second member about the second cantilever mount and a downward deflection of the spaced end of the first member causing a closing of the second member against the body member. With this arrangement as a garment is inserted into the garment retaining clip, the compound movement and action of the first and second members result in the garment receiving channel of the clip first opening to allow the garment to enter, and then closing to securely retain the garment therein and to prevent it from being accidentally dislodged therefrom.

In greater detail, each of the first and second members defines a rounded rectangular or oval shape having the same width W as the body member to resist movement into and out of the plane defined by the body member.

The present invention also provides a lightweight, molded plastic garment hanger comprising a hook member and a body member extending longitudinally from the hook member. The body member defines first and second opposite ends, and a garment retaining clip is integrally molded with the body member at each of the first and second ends. Each garment retaining clip comprises first and second opposed clip sides defining a garment receiving channel therebetween. The first clip side comprises a first downwardly extending member mounted to the end of the body member by a first cantilever mount and having a spaced end, and a second upwardly extending member integrally connected in spaced relation to the first member by a second cantilever mount and having a spaced free end. The second clip side comprises a downwardly extending member which is positioned opposed to and spaced from the first clip side to define the garment receiving channel therebetween. Pursuant to the present invention, the garment receiving channel defined by the first and second opposed clip sides proceeds from a bottom opening of the garment receiving channel, upwardly and inwardly towards the hook member to a top garment retaining position. The radial difference between the bottom opening and the top garment retaining position is approximately 0.125 inches, such that as a garment is inserted fully into the garment retaining clip, the length of the garment shrinks approximately ⅛" at each end of the garment hanger. This also means that the length of the garment must be expanded or stretched ¼", considering the expansion at both ends, to remove the garment from the garment retaining clip, which deters accidental dislodgement of the garment therefrom.

In greater detail, the first downwardly extending member of the first clip side includes a center stiffening rib extending longitudinally along the outer length of the first downwardly extending member to provide a relatively stiff and inflexible first downwardly extending member. Moreover, the first downwardly extending member of the first clip side further includes a center stiffening rib extending longitudinally along the inner length of the first downwardly extending member to provide a relatively stiff and inflexible first downwardly extending member.

BRIEF DESCRIPTION OF THE DRAWINGS

The foregoing objects and advantages of the present invention for a garment hanger may be more readily understood by one skilled in the art with reference being had to the following detailed description of a preferred embodiment thereof, taken in conjunction with the accompanying drawings wherein like elements are designated by identical reference numerals throughout the several views, and in which:

FIG. 3 is an enlarged view of one end of the lightweight, molded plastic garment hanger of FIGS. 1 and 2, illustrating further details of the novel features and construction thereof;

FIG. 4 is an enlarged sectional view, taken along sectional arrows 4—4 in FIG. 3, and illustrates further details of construction of the first and third garment clips of the garment hanger;

FIG. 5 is an enlarged sectional view, taken along sectional arrows 5—5 in FIG. 3, and illustrates further details of construction of the second garment clip of the garment hanger;

FIG. 6 is a front elevational view of the first garment clip with a garment strap being inserted into the mouth of the clip, and illustrates how the initial insertion causes the clip to deform to accept the garment strap;

DETAILED DESCRIPTION OF THE DRAWINGS

Figure 1:
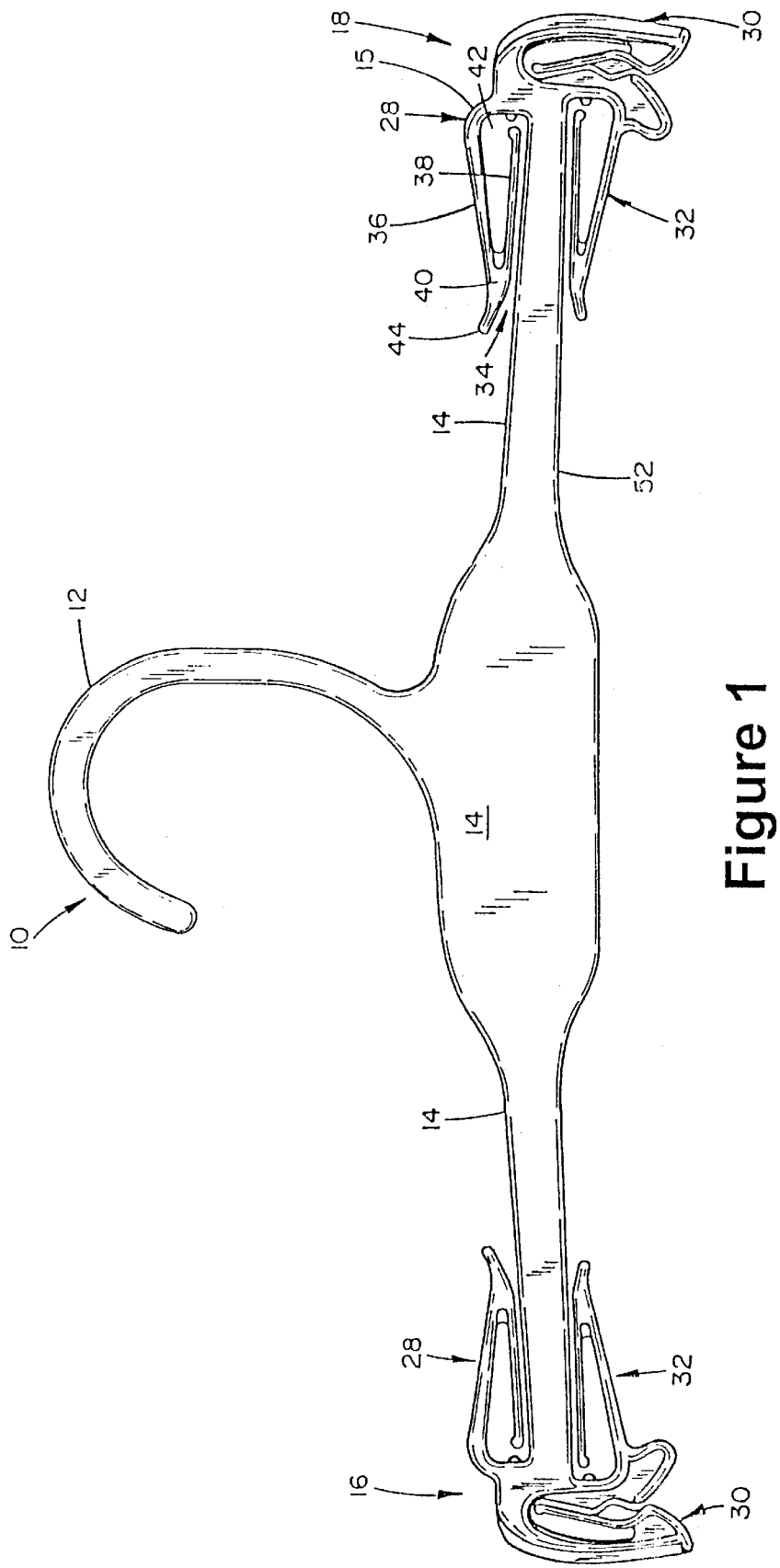
FIG. 1 is a front elevational view of a preferred embodiment of a lightweight, molded plastic garment hanger pursuant to the teachings of the present invention.
Figure 2:
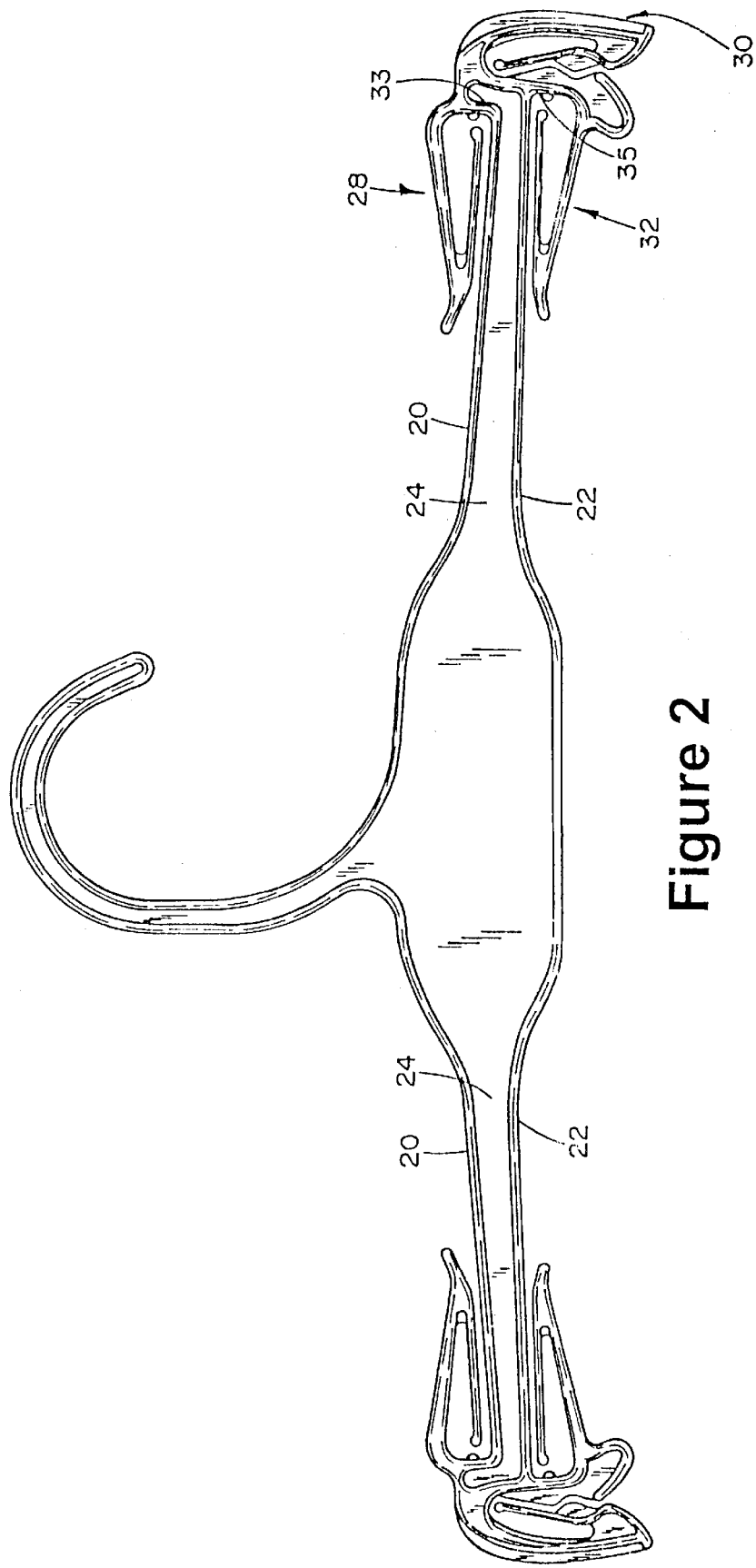
FIG. 2 is a rear elevational view of the lightweight, molded plastic garment hanger illustrated in FIG. 1.

Referring now in detail to the drawings, FIGS. 1 and 2 illustrate respectively front and rear elevation views of a molded plastic garment hanger 10 having a central hook member 12 which is integrally molded with an elongated hanger body 14, the latter of which includes a pair of coplanar oppositely directed ends 16 and 18, with each of the ends defining a plurality of garment retaining clips for suspending one or more garments. The particular illustrated shapes of the central hook member 12 and elongated hanger body 14 are exemplary only, and can have various and different shapes and dimensions. The shaded areas in FIG. 3 are all formed with a reduced width w, reduced from the full width W, as illustrated in FIGS. 4 and 5.

As depicted best in FIGS. 1, 2 and 4, to maximize strength while using the minimum amount of material, the hanger body 14 and the central hook member 12 are constructed with a C-shaped cross-section having a first horizontally extending flange 20 and a second horizontally extending flange 22 connected by a vertical wall 24. However, in alternative embodiments the hanger body 14 may be constructed with a curved M-shaped cross-section, an E-shaped cross-section, an I-beam cross-section, or any suitable cross-section which may improve the strength to weight ratio for particular applications to resist flexing due to the weight of the garment hanging from the hanger of the present invention and to assist in maintaining the hanger upright when in use.

The plurality of garment retaining clips can include one or more of a first garment retaining clip 28, a second garment retaining clip 30, and a third garment retaining clip 32. The first garment retaining clip 28 is generally horizontally disposed above the body member 14. The second garment retaining clip 30 is generally vertically disposed, with an inward slant as described in greater detail hereinbelow, and is disposed outwardly from the end 16 or 18. The third garment retaining clip 32 is generally horizontally disposed below the hanger body 14. The horizontally disposed garment retaining clips 28 and 32 typically receive shoulder straps from a brassiere, slip or like garment. The generally vertically disposed second garment retaining clip 30 typically receives a waistband from panties, swimsuit bottoms or like garments.

The hanger body 14 is constructed with a C-shaped cross-section having a generally flat central section 24 and reinforcing flanges 20, 22 extending around the edges of the central section which define the width of the garment hanger. The primary support members of the plurality of garment retaining clips 28, 30 and 32 are generally constructed of the same width W as the reinforcing flanges 32, as described in further detail hereinbelow. As illustrated in FIG. 2, the top flange 20 extends upwardly at 33 and continuously into the structure of the first garment retaining clip 28 and one side of the second garment retaining clip 30, which have the same width W as the flange 33. The bottom flange 22 extends downwardly at 35 and continuously into the structure of the third garment retaining clip 32 and the second side of the second garment retaining clip 30, which also have the same width W as the reinforcing flange.

As illustrated in FIGS. 1–3, the first garment retaining clip 28, which is positioned above and adjacent to the body member 14, defines a first garment receiving channel or mouth 34 therebetween. The first garment receiving clip 28 has a resilient substantially V-shaped, double return configuration comprising a first elongated member 36 and a second elongated member 38 integrally connected in a spaced V-shaped relationship by a connecting portion 40. When a garment is inserted into the first garment receiving channel 34, the second elongated member 38 deflects into a deflecting area 42 while it serves to hold the garment in place. The deflecting area 42 is defined by the first elongated member 36, the second elongated member 38 and the connecting portion 40. The first garment retaining clip 28 is designed and configured such that the second member 38 is moveable in a direction transverse to and from the body member 14 while resisting movement into and out of the plane of the hanger body 14. To facilitate the insertion of a garment to be suspended from the hanger, the connecting portion 40 is formed with a rounded lip 44 which extends upwardly and inwardly toward the hook member 12.

The first garment retaining clip 28, with the V-shaped members 36, 38, provides a construction having two primary resilient mounts, the first resilient mount being the cantilever mounting at 46 of the first member 36, and the second resilient mount being the cantilever mounting at 40 of member 38 relative to member 36. The construction of the first and second members 36, 38 is further illustrated in FIG. 4, which illustrates the rounded rectangular or oval shape of each of the first and second members 36, 38.

The first and second members 36, 38 are both constructed to have the same width W as the hanger body 14, which resists movement of the members 36, 38 into and out of the plane of the hanger body. This is in contrast to a prior art design in which a member similar to member 38 was constructed with a reduced width, which resulted in substantial movement of the member into and out of the plane of the hanger body. FIGS. 3 and 4 also illustrate a center stiffening rib 50 connecting the first and second members 36 and 38 near the cantilever mounting 40 which stiffens the cantilever mounting, and also resists movement of member 38 into and out of the plane of the hanger body.

The construction and design is such that as a garment or strap is initially inserted into the mouth of the first garment receiving channel 34, as illustrated in FIG. 6, an initial expansion at the mouth of the garment receiving channel caused by insertion of the garment therein causes a rotation of the combination of the first and second members 36, 38 about the first cantilever mount 46. As illustrated in FIG. 6, during the initial insertion the first member 36 bends upwardly, with the upward bend most pronounced nearer to the cantilever mounting at 46. As the garment or strap slides past the second cantilever mount 40 and towards the free end 48 of the second member 38, as illustrated in FIG. 7, it causes an upward flexure of the free end 48 of the second member 38, which also results in a downward deflection of the free end of the first member 36 at 40 and a closing of the bottom of the second member 38 near the location at 40 relative to the hanger body 14 positioned therebeneath.

Figure 7:
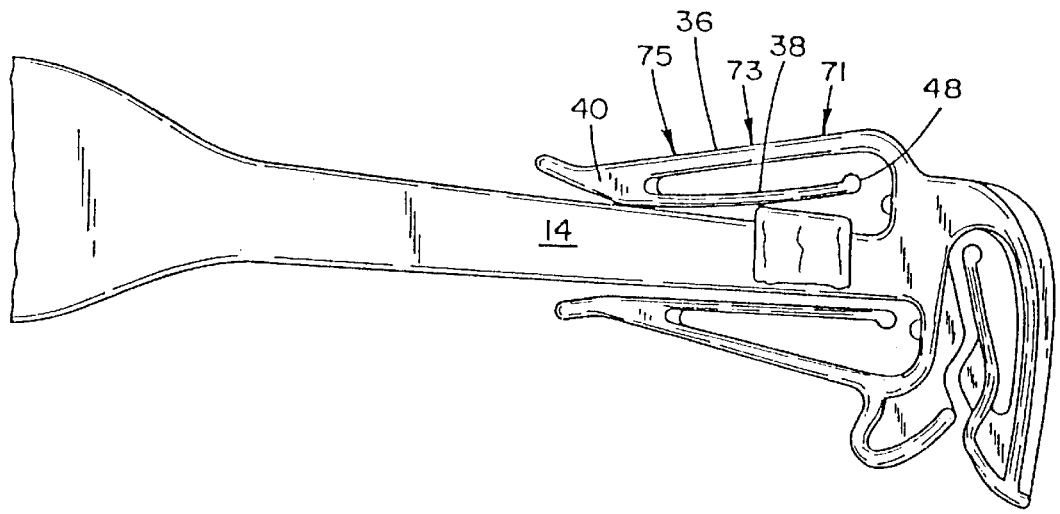
FIG. 7 is a front elevational view of the first garment clip with a garment strap fully inserted therein, and illustrates how the full insertion causes the free end of the first garment clip to close against the garment therein, thereby securely retaining the garment in the clip.
Figure 8:
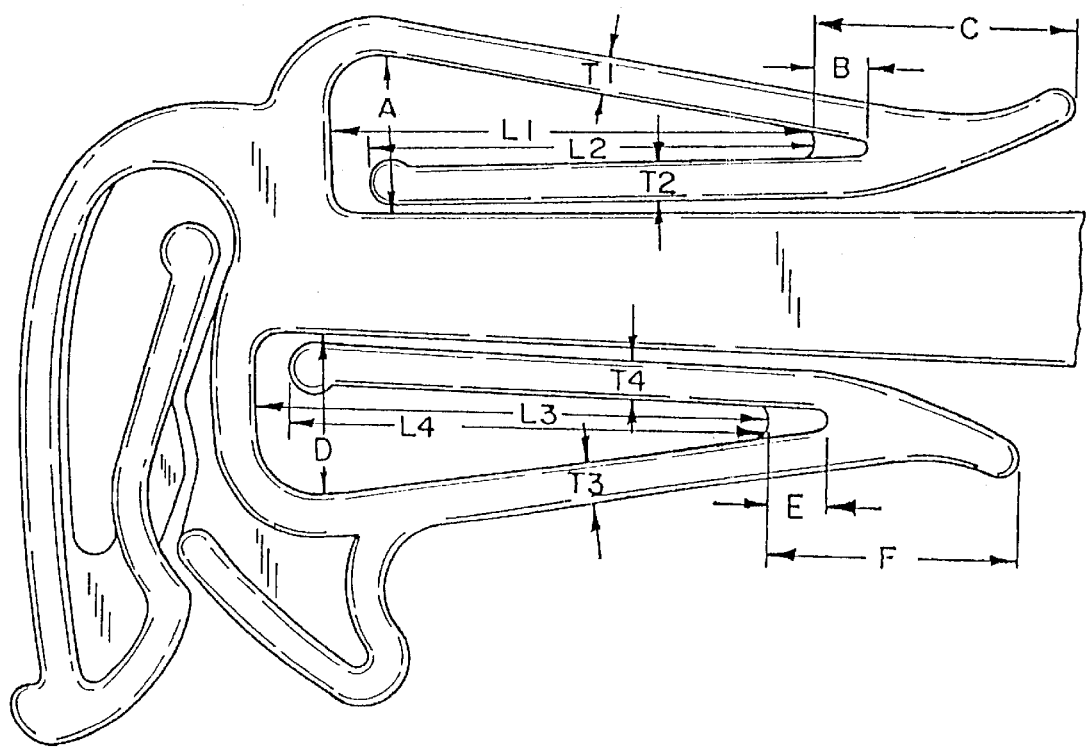
FIG. 8 is a front elevation view of the first and third garment clips, and illustrates some of the more significant dimensions of those clips.

As illustrated in FIG. 7, when the garment clip is closed upon a garment, the top member 36 frequently assumes a complex curved shape, initially bowing downwardly at 71, and then bowing up very slightly at 73, then bowing continuously downwardly at 75 towards the connecting position 40.

Accordingly, as a garment or strap is inserted into the first garment retaining clip 28, the compound mounting and action of the first and second members 36, 38 result in the mouth of the clip first opening to allow the garment to enter, and then closing to securely retain the garment or strap therein to prevent it from being accidentally dislodged and falling from the first garment retaining clip. This advantageous feature of automatic closing of the mouth of the garment retaining clip against a garment or strap after the garment or strap has been inserted therein is novel relative to known prior art garment retaining clips.

Moreover with such molded plastic garment hangers, garments are frequently inserted into the garment clips manually by a person who inserts a great number of garments into a corresponding number of garment clips. Prior art garment clips have been designed with additional strength and stiffness to prevent breakage of the garment clips as a garment is inserted therein or removed therefrom. The additional strength and stiffness has often been achieved by designing the moveable arm or arms of the garment clip with a stiffening, reinforcing outer rib extending longitudinally along the outer length of the moveable arm, similar to the reinforcing outer rib 58 of the garment clip 30 illustrated in FIGS. 3 and 5. With the stiffer, more rigid clips typical of the prior art, the persons inserting the garments into the garment clips frequently developed carpel tunnel syndrome because of the constant strain associated with inserting a large number of garments, particularly thicker garments, into the garment clips.

The present invention takes an opposite approach in which the garment clip is designed with greater flexibility, without a stiffening rib extending longitudinally along the length of the moveable clip arm. The more flexible clip arm is much easier to open and use by a customer, and moreover the greater flexibility results in almost no breakage of the clip arms. The greater flexibility is achieved by eliminating a stiffening rib, and also by designing the garment clip with a double return configuration as explained hereinabove.

The garment retaining clip of the present invention is designed to be much more flexible and easier to open and use than previous prior art designs. The more flexible design is achieved by the double return configuration and functioning of the garment clip as described hereinabove, and by a careful designing of, the garment dimensions, ratios of the dimensions, and selection of an appropriate material.

The inventive plastic hanger can be formed of styrene which provides a clear, virtually transparent polystyrene hanger for maximum display of intimate apparel garments, such as bras and panties, to be suspended therefrom. In the alternative, the hanger can be molded from polypropylene; preferably II.I, styrene polypropylene; polypropylene; polyvinychloride; ABS or other suitable thermoplastics and mixtures thereof. For additional reinforcement, K resin can be added to the plastic material.

The preferred material polystyrene has a Flexural Modulus, MPa, of 3,170, taken from CONCISE ENCYCLOPEDIA OF POLYMER SCIENCE AND ENGINEERING, p. 1117.

In one preferred embodiment, the first garment clip 28 has the following dimensions shown in the left column, which can vary in alternative embodiments between the lower and upper limits shown respectively in the middle and right columns,

| | | |
|---|---|---|
| W = 0.190" | 0.14 | 0.24 |
| $T_1 = T_2 = 0.078$" | 0.06 | 0.10 |
| $L_1 = 0.890$" | 0.67 | 1.11 |
| $L_2 = 0.807$" | 0.60 | 1.01 |
| A = 0.318" | | |
| B = 0.130" | | |
| C = 0.414" | | |

The garment clip 28 has the following ratios of dimensions shown in the left column, which can vary in alternative embodiments between the lower and upper limits shown respectively in the middle and right columns.

| | | |
|---|---|---|
| W/T = 2.436 | 1.8 | 3.0 |
| $L_1/T$ = 11.410 | 8.5 | 14.3 |
| $L_2/T$ = 10.346 | 7.7 | 13.0 |

-continued

| | | |
|---|---|---|
| $L_1/W = 4.684$ | 3.5 | 5.9 |
| $L_2/W = 4.247$ | 3.2 | 5.3 |

The third garment retaining clip 32 is constructed similar to the first garment retaining clip 28, and accordingly functions in a manner similar to that explained above for the first garment retaining clip.

The third garment clip 32 has the following dimensions, shown in the left column, which can vary in alternative embodiments between the lower and upper limits shown respectively in the middle and right columns

| | | |
|---|---|---|
| W = 0.190" | 0.14 | 0.24 |
| $T_3 = T_4 = 0.078"$ | 0.06 | 0.10 |
| $L_3 = 0.950"$ | 0.71 | 1.19 |
| $L_4 = 0.876"$ | 0.66 | 1.11 |
| D = 0.321" | | |
| E = 0.130" | | |
| F = 0.363" | | |

The third garment clip 32 has the following ratios of dimensions shown in the left column, which can vary in alternative embodiments between the lower and upper limits shown respectively in the middle and right columns

| | | |
|---|---|---|
| W/T = 2.436 | 1.8 | 3.0 |
| $L_3/T = 12.179$ | 9.1 | 15.2 |
| $L_4/T = 11.231$ | 8.4 | 14.0 |
| $L_3/W = 5.000$ | 3.8 | 6.2 |
| $L_4/W = 4.611$ | 3.5 | 5.8 |

The above dimensions and ratios have been found to provide garment clips constructed of polystyrene which are particularly efficacious and useful. However, other suitable plastic materials having a different Modulus of Elasticity (Young's Modulus) than polystyrene may be utilized in alternative embodiments with suitable modifications of the garment clip dimensions and ratios of dimensions.

Referring to FIG. 3, the second garment retaining clip 30 is integrally molded with the hanger body at each of the first and second ends. Each second garment retaining clip comprises first and second opposed clip sides defining a garment receiving channel 52 therebetween. The second garment retaining clip 30 is designed to mount panties, and includes several novel features. The V at 53 defining the mouth of the garment receiving channel 52 of the second garment retaining clip defines a larger opening than the mouths of known prior art garment retaining clips, which makes it easier to mount panties on the garment hanger. The first clip side comprises a first downwardly extending support member 54 mounted to the end of the body member by a first cantilever mount at 55 and having a spaced end. The construction of the first support member 54 of the panty holder is also novel, and provides a relatively inflexible mount for the outer rib, which provides a relatively stiff and inflexible support as a panty band is inserted into the second garment retaining clip.

The first support member 54 has a rounded rectangular shaped member 56, as illustrated in section in FIG. 5, having the same width W as the hanger body 14. Additionally, a center stiffening rib 58 extends longitudinally along the outer length of support member 54. The first support member 54 extends to a spaced end at 60 which forms a cantilever support and mount for a second support member 62. The second member 62 also has a rounded rectangular shape, as illustrated in section in FIG. 5, having the same width W as the hanger body. A center rib 64 extends longitudinally along the inner length of support member 56, and extends into a center cantilever support 66 for the second member 62. The second member 62 defines a center toothed section 68.

The second clip side comprises a downwardly extending member which is positioned opposed to and spaced from the first clip side to define the garment receiving channel 52 therebetween. The reinforcing flange 22 of the hanger body 14 extends downwardly at 70 into a support member 72, having the same width W, which extends downwardly to form the second opposed side of the second garment retaining clip. The support member 72 extends downwardly, and then inwardly at 74 where it extends into and forms a part of the third garment retaining clip 32. A support member 76, having a width W, extends downwardly from support member 72, and then curves around and extends outwardly at 78. A center rib 80 defines a center toothed section 82, spaced and opposed to the center toothed section 68, to form the garment receiving channel 52 therebetween to grasp and retain a garment therein.

A further novel feature of the second garment retaining clip is the inward slant defined by the garment receiving channel 52 of the panty retaining clip. As a panty waist band is inserted into the second garment retaining clip and is inserted from an initial position at location 86 to a fully inserted position at location 88, the panty waist band moves radially inwardly towards the center of the garment hanger a distance d, FIG. 6, of approximately ⅛ inch. This means that after a panty waist band is inserted fully into the panty retaining clip, the panty waist band shrinks approximately ⅛" at each end of the garment hanger. This also means that the panty waist band must be expanded or stretched ¼", ⅛" at each end of the garment hanger, to remove the panty from the panty retaining clip, which makes accidental removal or dislodgement of the garment from the garment clip a virtual impossibility.

A novel feature of the second garment retaining clip 30 is the reinforcing outer rib 58 which extends along the length of and reinforces the first support member 58 to make the first support member more rigid and less resilient, and also the inner reinforcing rib 64.

Figure 9A:
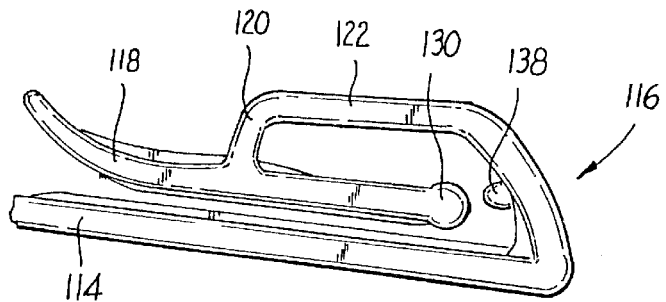
FIG. 9(a) is a front elevation view of the prior art clip design illustrated in U.S. Pat. No. 5,632,423, and corresponds to FIG. 19 of that patent.
Figure 9B:
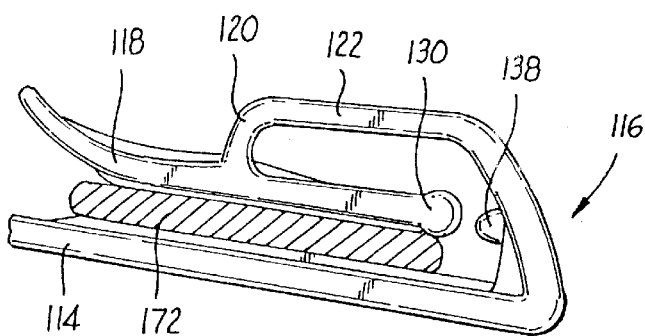
FIG. 9(b) is a front elevation view of the prior art clip design illustrated in U.S. Pat. No. 5,632,423, and corresponds to FIG. 21 of that patent.

FIGS. 9(a) and 9(b) illustrate a known prior art design, and correspond to FIGS. 19 and 21 of U.S. Pat. No. 5,632,423. As described in that patent, the clip includes a pressing beam 118 which is substantially centrally supported by a carrier 120. The carrier 120 is supported by a spring arm 122 and a curved connecting part 124 mounted on the body of the hanger, depicted generally as bar 114. A stop formation or stop element 138 is positioned "substantially in alignment" with the pressing beam 118. According to the teaching of U.S. Pat. No. 5,632,423, the purpose of the stop formation is "to keep the garment in the proper position and prevent the garment from moving around the curved head 130 and into the gap between the arm 122 and the beam" or pressing member 118.

Figure 9C:
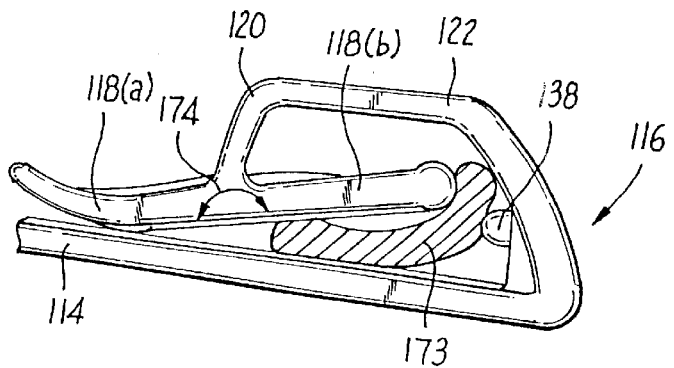
FIG. 9(c) is a front elevation view of the clip design illustrated in U.S. Pat. No. 5,632,423, and illustrates the problem solved by the present invention.

As illustrated in prior art FIG. 9(b) a garment strap 172 has been inserted into the garment clip, with the pressing member 122 parallel to the bar or body member 114. This is an illustrative example of the manner in which this clip functions with a relatively wide brassiere strap, as the one depicted at 172. However it has been found, that when a clip that is "substantially aligned" with the pressing member is used with a narrow garment strap, as illustrated in prior art FIG. 9(c), a different problem appears. When the strap 173 first encounters the pressing member 118, the first end 118(a) of pressing member lifts, and the pressing member 118 rotates clockwise as illustrated in FIG. 20 of U.S. Pat. No. 5,632,423, and as further illustrated by arrow 174 of FIG. 9(c). However, if the strap 173 is pulled towards the second end 118(b) of the pressing member, and passes beyond the support element 120, the pressing member may rotate counterclockwise to the position illustrated in FIG. 9(c). When this happens, the end 130 can be rotated above the stop formation 138, allowing the garment strap 173 to slip therebetween, and into the gap between the arm 122 and the pressing member 118. Once a strap has passed into this space, it is very difficult to remove, After the strap has passed completely into the gap space 175, the resilience of the plastic at support 120 will return the pressing member to its original position, adjacent the stop formation 138, closing the gap therebetween, and making removal of the strap without damage to the clip or the strap very difficult.

Figure 10A:
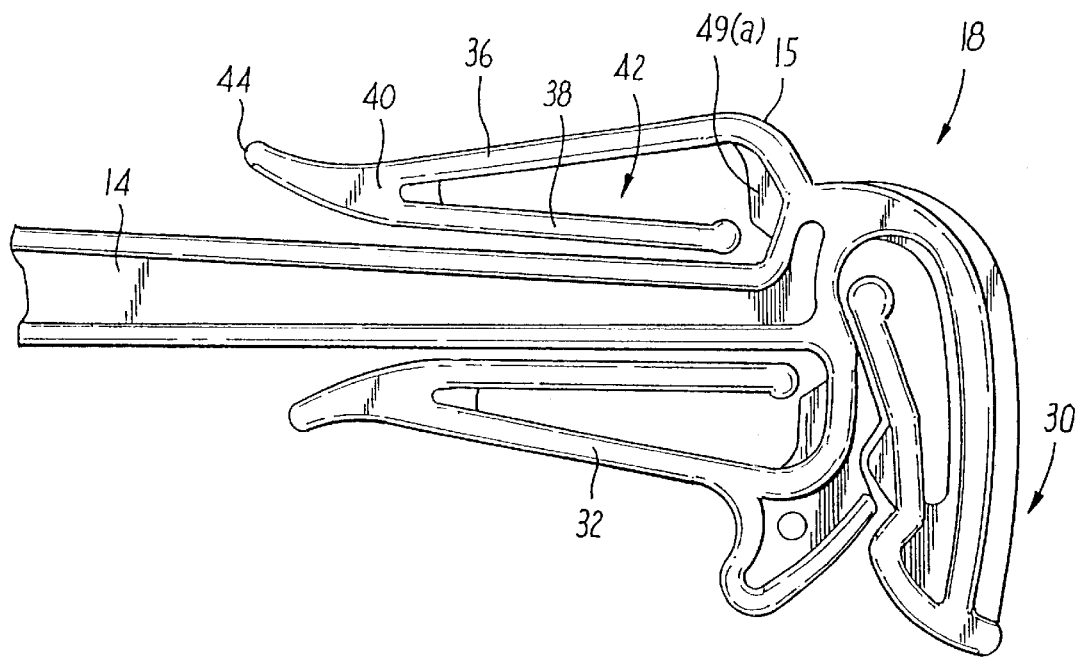
FIG. 10(a) is a front elevation view of the clip design illustrating one embodiment of a new and improved stop formation which prevents the migration of straps around the inner arm of the garment retaining clip.
Figure 10B:
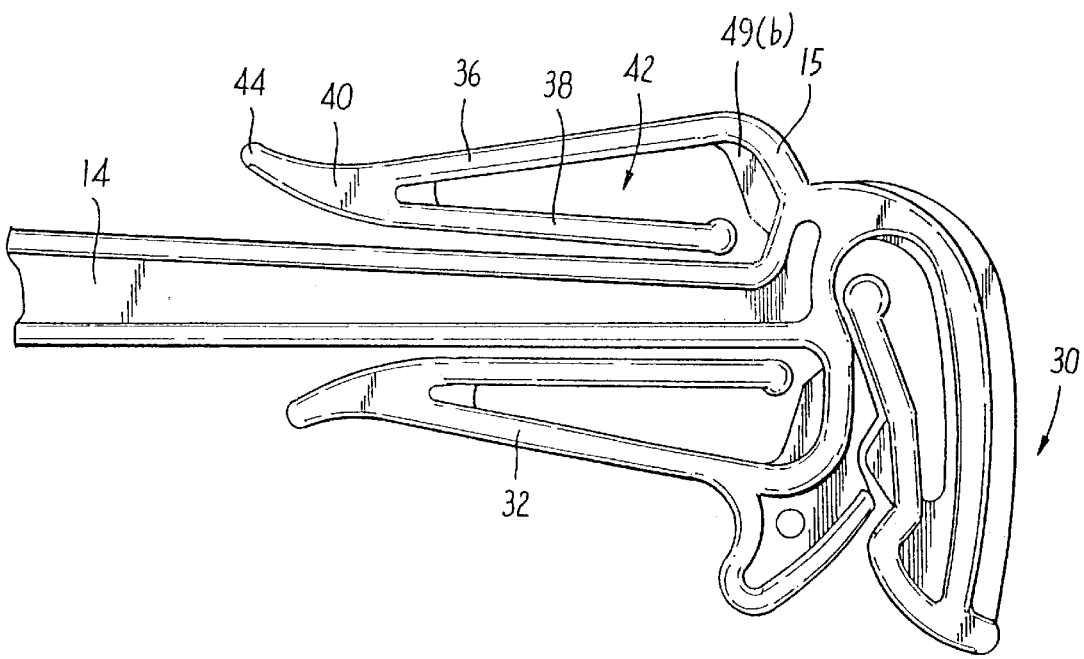
FIG. 10(b) is a front elevation view of the clip design illustrating a second embodiment of a new and improved stop formation which prevents the migration of straps around the inner arm of the garment retaining clip.
Figure 10C:
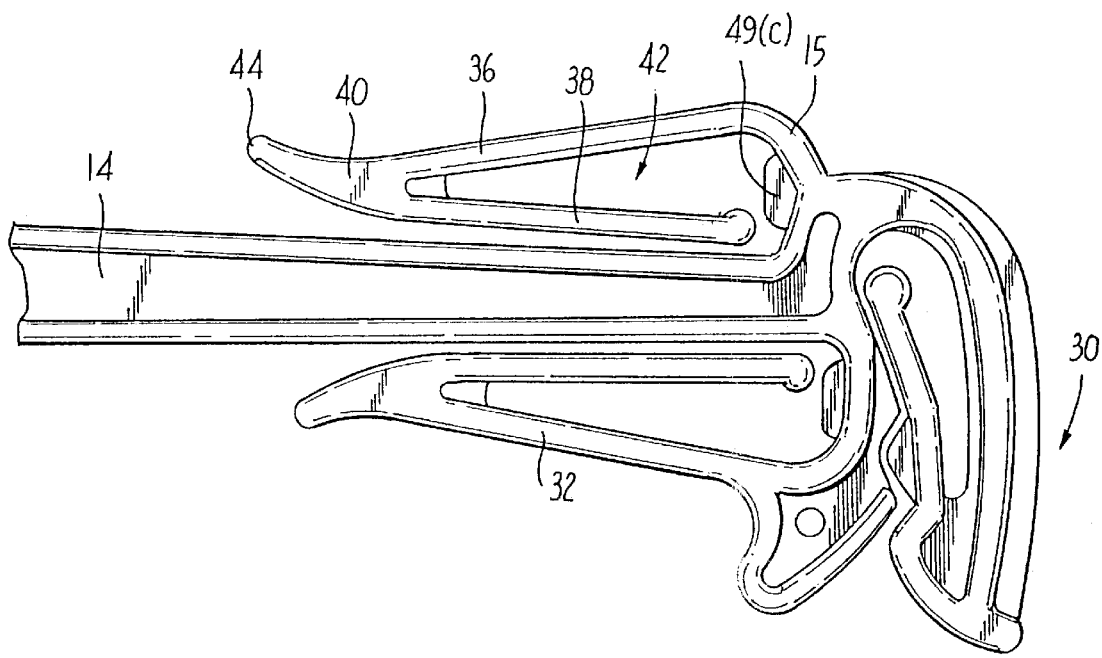
FIG. 10(c) is a front elevation view of the clip design illustrating a third embodiment of a new and improved stop formation which prevents the migration of straps around the inner arm of the garment retaining clip.

The present invention describes an improved stop formation, illustrated at 49(a), 49(b), 49(c) and 49(d) in FIGS. 10(a), 10(b), 10(c) and 10(d) respectively. This stop formation is not located "substantially adjacent" the end of the pressing member of FIGS. 9 or the inner arm 38 of FIGS. 10; Instead, it is located above the inner arm 38, along the trajectory of the outer end of the inner arm, so as to block access along a predefined portion of a path or trajectory described by the end of the inner arm 38, as it flexes upwardly in response to the presence of a narrow strap. By moving the stop formations 49 upwardly, they block access to the inner space 42, when the inner arm 38 is flexed upwardly. Further, by blocking access along a predefined portion of the path, rather than at a specific tangential point, as taught by the prior art, the performance of the stop formation is improved. The surface of the stop formation may be a linear web, as illustrated by FIG. 10(a), a curved web which follows the trajectory of a flexing inner arm 38, as illustrated in FIG. 10(b), or an elongated bump, as illustrated in FIG. 10(c).

Figure 10D:
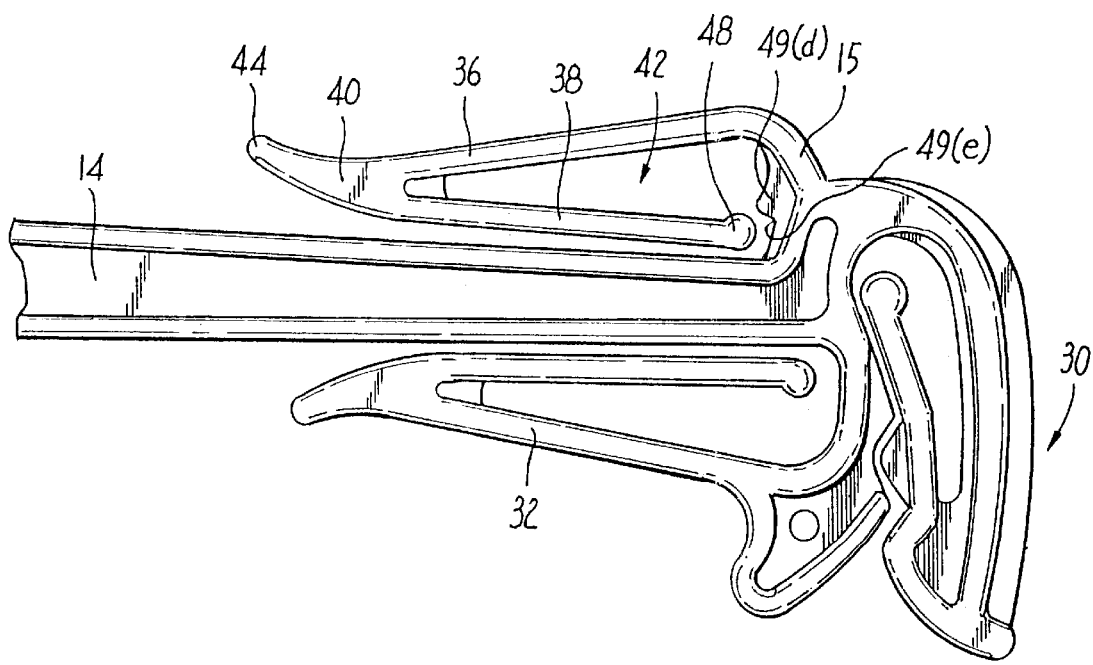
FIG. 10(d) is a front elevation view of the clip design illustrating a fourth embodiment of a new and improved stop formation which prevents the migration of straps around the inner arm of the garment retaining clip.

Alternately, a continuous web 49(d), with a reverse cut out 49(e) "substantially aligned" with the inner arm, as illustrated in FIG. 10(d) may be employed. If the inner arm is formed with a rounded tip, such as the tip 48 illustrated in the drawings, the reverse cut may mirror the shape of the tip. If a thin web is employed for the stop formation, the inwardly projecting formation, formed above the reverse cut out, may be dimensioned to slightly touch the tip 48 as it is flexed upwardly.

As is apparent from a review of the various embodiments illustrated in FIGS. 10(a) to 10(d), the new and improved stop formations are not "substantially aligned" with the inner arm 38. While several embodiments and variations of the present invention for a garment hanger are described in detail herein, it should be apparent that the disclosure and teachings of the present invention will suggest many alternative designs to those skilled in the art.

What is claimed is:

1. A molded plastic garment hanger comprising:
   a. A central hook member, said central hook member being vertically disposed;
   b. An elongated body member horizontally disposed and integrally molded to said hook member;
   c. A first horizontal garment retaining clip being disposed adjacent to the body member comprising;
      i. A primary support member, integrally connected to said body member and vertically extending away from said body member;
      ii. A first elongated member extending toward said body member and away from said primary support member;
         1. A cantilever mount for connecting said primary support member to said first elongated member;
      iii. A second elongated member, disposed closer to the body member than the first elongated member, horizontally extending toward said primary support member; and
         1. A connecting portion for connecting the said first elongated member to said second elongated member, having a tip being curved away from said body member; and
      iv. A mouth defined by the surfaces between said tip and said body member for guiding a garment into said horizontal garment retaining clip;
      v. Wherein said cantilever mount and said elongated member have the same width (W), and the same W to thickness (T) ratio where the W to T ratio is greater than 1.8 and less than 3.0 and permits flexure between said cantilever mount and said connection portion.

2. The hanger of claim 1 comprising;
   a. A vertical garment retaining clip being disposed outwardly from said body member comprising:
      i. A first support member, vertically extending from said body member;
      ii. A vertically extending member having a free end extending away from said body;
         1. A first cantilever mount connecting the end of said first support member to said vertically extending member;
      iii. A second support member, extending from said body member in a direction that is vertically opposed from said cantilever mount;
         1. Said second support member curving toward said vertically extending member at a predetermined vertical distance from said body member;
      iv. A mouth defined by the surfaces between said free end of said vertically extending member and said second support member for guiding a garment into said vertical garment retaining clip.

3. The hanger of claim 1 wherein said body member comprises:
   a. A C-shaped cross section having a central web member and a plurality of flange members, said flange members defining a top flange member and bottom flange member at opposing vertical ends, said flange members being horizontally disposed along the length of the body member;
      i. Wherein said primary support member, said first elongated member and at least one of said plurality of flange members are integrally connected to form a first continuous member; wherein
         1. said first continuous member has a constant width.

4. The hanger of claim 3 wherein:
   a. Said second elongated member and said first continuous member have a constant width.

5. The hanger of claim 3 wherein the second support member of said vertical garment retaining clip has the same width as said first continuous member.

6. The hanger of claim 1 wherein the horizontal garment retaining clip comprises a center rib, disposed at the connecting portions between the first and second elongated members.

7. The hanger of claim 2, wherein said vertical garment retaining claim comprises:

a. A support member, outwardly disposed along the length of said first vertically extending member.

8. The hanger of claim 2, wherein said vertical garment retaining clip comprises:
   a. A second vertically extending member disposed between said first vertical member and said second support member.
   b. A second cantilever mount connecting the free end of said vertically extending member to said second vertically extending member;
   c. A garment receiving channel defined by the surfaces between the second vertical member and said second support member.

9. The hanger of claim 8 wherein:
   a. Said second vertically extending member of said vertical clip comprises a first ribbed section;
   b. Said second support member comprises a second ribbed section; and
   c. Wherein a free edge of said first ribbed section opposes a free edge of said second ribbed section so that said garment receiving channel grasps and retains a garment.

10. The hanger of claim 3 wherein said first horizontal garment retaining clip is disposed above said body member, said hanger further comprising:
    a. A second horizontal garment retaining clip being disposed below the body member comprising;
       i. A primary support member, integrally connected to said body member and said second support member to form a second continuous member, said primary support member vertically extending away from said body member;
       ii. A first elongated member extending toward said body member and away from said primary support member;
          1. A cantilever mount integrally connecting the end of said second support member of said vertical clip;
       iii. A second elongated member, disposed closer to the body member than the first elongated member, horizontally extending toward said primary support member; and
          1. A connecting portion for connecting the said first elongated member to said second elongated member having a curved tip extending away from said body member; and
       iv. A mouth defined by the surfaces between said tip and said body member for guiding a garment into said horizontal garment retaining clip;
       v. Wherein said cantilever mount and said first elongated member have the same width (W), and the same W to thickness (T) ratio, where the W to T ratio is greater than 1.8 and less than 3.0 and permits flexure between said cantilever mount and said connection portion.

11. The hanger of claim 9 wherein said second continuous member, said cantilever mount of said second horizontal clip, said first elongated member of said second horizontal clip and said tip of said second horizontal clip have the same width.

12. The hanger of claim 10 wherein said second continuous member and said second elongated member of said second horizontal clip have the same width.

13. The hanger of claim 11 wherein said first and said second continuous members have the same width.

14. The hanger of claim 12 wherein said horizontal clips comprise a center rib, disposed at the connecting portions between the first and second elongated members.

15. The hanger of claim 1 or 9 where said connecting portion and second elongated member have a W to T ratio that permits flexure between said connecting portion and a free end of said second elongated member.

16. The hanger of claim 3 or 4 or 10 or 11 wherein:
    a. The W to T ratio is between 1.8 and 3.0;
    b. The Length (L) to T ratio of said first elongated member is between 8.5 and 14.3;
    c. The L to T ratio of the second elongated member is between 7.7 and 13.0;
    d. The L to W ratio of said first elongated member is between 3.5 and 5.9; and
    e. The L to W ratio of said second elongated member is between 3.2 and 5.3.

17. The hanger of claim 10 or 11 wherein:
    a. The W to T ratio is between 1.8 and 3.0;
    b. The Length (L) to T ratio of said first elongated member of said second clip is between 9.1 and 15.2;
    c. The L to T ratio of the second elongated member of said second clip is between 8.4 and 14.0;
    d. The L to W ratio of said first elongated member of said second clip is between 3.8 and 6.2; and
    e. The L to W ratio of said second elongated member of said clip is between 3.8 and 5.8.

* * * * *